(12) United States Patent
Tubb (10) Patent No.: US 10,754,926 B2
(45) Date of Patent: Aug. 25, 2020

(54) DATA MANAGEMENT UNIT AND METHOD OPERATING SAME

(71) Applicant: Sanofi-Aventis Deutschland GMBH, Frankfurt am Main (DE)

(72) Inventor: Andrew Tubb, Paris (FR)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 464 days.

(21) Appl. No.: 15/022,146

(22) PCT Filed: Sep. 19, 2014

(86) PCT No.: PCT/EP2014/070003
§ 371 (c)(1),
(2) Date: Mar. 15, 2016

(87) PCT Pub. No.: WO2015/040165
PCT Pub. Date: Mar. 26, 2015

(65) Prior Publication Data
US 2016/0239628 A1  Aug. 18, 2016

(30) Foreign Application Priority Data
Sep. 20, 2013  (EP) ..................... 13185395

(51) Int. Cl.
| | |
|---|---|
| *G01N 33/48* | (2006.01) |
| *G06F 19/00* | (2018.01) |
| *G16H 40/63* | (2018.01) |
| *G16H 10/60* | (2018.01) |
| *G16H 20/17* | (2018.01) |
| *G16H 50/20* | (2018.01) |
| *A61B 5/145* | (2006.01) |
| *A61B 5/00* | (2006.01) |

(52) U.S. Cl.
CPC ...... *G06F 19/3418* (2013.01); *A61B 5/14532* (2013.01); *A61B 5/7221* (2013.01); *G16H 10/60* (2018.01); *G16H 20/17* (2018.01); *G16H 40/63* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 7,570,980 B2 | 8/2009 | Ginsberg | |
| 2007/0254593 A1* | 11/2007 | Jollota | A61B 5/14532 455/67.11 |
| 2008/0194934 A1 | 8/2008 | Ray et al. | |
| 2009/0253970 A1* | 10/2009 | Bashan | A61B 5/14532 600/316 |
| 2010/0152554 A1 | 6/2010 | Steine et al. | |
| 2011/0257496 A1 | 10/2011 | Terashima et al. | |
| 2012/0109687 A1 | 5/2012 | Tubb | |
| 2012/0173151 A1* | 7/2012 | Galley | G06F 19/325 702/19 |

(Continued)

FOREIGN PATENT DOCUMENTS

| | | |
|---|---|---|
| EP | 2085029 | 8/2009 |
| EP | 2537467 | 12/2012 |

(Continued)

OTHER PUBLICATIONS

International Preliminary Report on Patentability in International Application No. PCT/EP2014/070003, dated Mar. 22, 2016, 8 pages.
International Search Report and Written Opinion in International Application No. PCT/EP2014/070003, dated Dec. 3, 2014, 10 pages.
Rote Liste, "50. Hypophysen-, Hypothalamushormone, andere regulatorische Peptide u. ihre Hemmstoffe," Chapter 50, ed. 2008, 20 pages.
Wood et al., "Habits in Everyday Life: Thought, Emotion, and Action," Journal of Personality and Social Psychology 83(6):1281-1297, Dec. 2002.

*Primary Examiner* — Anna Skibinsky
(74) *Attorney, Agent, or Firm* — Fish & Richardson P.C.

(57) ABSTRACT

The present invention refers to data management unit comprising a data storage (130) adapted to store a plurality of measurement values of the physiological parameter, preferably a blood glucose level, for each measurement value an associated event tag, for each measurement value an associated time stamp, an associated time range for tagging preselection for each of at least two meal events, each time range is preferably user-settable, preferably also for a fasting event an associated time range for tagging preselection, this time range is preferably user-settable, a processor (140) adapted to receive a new measurement value from the data storage (130) or from a measurement unit (110), which is preferably at least shortly connected for data transfer, assign an associated time stamp to the new measurement value, if an associated time stamp does not yet exist with the new measurement value, receive selection data containing the information that the user has selected and/or confirmed one of a "before meal" tag and an "after meal" tag with regard to the new measurement value, automatically select an additional associated tag referring to one of the at least two meal events and preferably also of the fasting event based on the selection data and on a comparison of the time stamp of the new measurement value with the associated time ranges for tagging preselection of the at least two meal events and preferably also with the time range for tagging preselection of the fasting event. The invention further refers to a corresponding medical device (100), a corresponding method and computer program for operating a data management unit as well as to a corresponding computer program product.

18 Claims, 4 Drawing Sheets

(56) References Cited

U.S. PATENT DOCUMENTS

2012/0232520 A1* 9/2012 Sloan ................ A61B 5/14532
604/504
2012/0266251 A1 10/2012 Birtwhistle et al.
2014/0148668 A1* 5/2014 Chovanda ............. A61B 5/743
600/347

FOREIGN PATENT DOCUMENTS

| JP | 2008-197102 | 8/2008 |
| JP | 2012-516735 | 7/2012 |
| JP | 2013/017808 | 1/2013 |
| WO | WO 2010/089307 | 8/2010 |
| WO | WO2011/007051 | 1/2011 |
| WO | WO 2010/052849 | 4/2012 |

* cited by examiner

DATA MANAGEMENT UNIT AND METHOD OPERATING SAME

CROSS-REFERENCE TO RELATED APPLICATIONS

This application is a U.S. national stage application under 35 USC § 371 of International Application No. PCT/EP2014/070003, filed on Sep. 19, 2014, which claims priority to European Patent Application No. 13185395.4, filed on Sep. 20, 2013, the entire contents of which are incorporated herein by reference.

The present invention relates to a data management unit, a medical device, preferably a glucose meter, a method for operating same, a respective computer program and a computer program product.

The following description of the invention mainly refers to diabetes as a health problem and the blood glucose level as the physiological parameter to be controlled in order to assess the effectiveness of the prescribed treatment. However, the invention may also be used with regard to other health problems and for management of other physiological parameter data like (a) blood pressure in hypertensive heart disease, (b) cholesterol or lipoprotein profile in patients with risk factors for heart disease and stroke, (c) peak flow in asthmatic patients, or (d) coagulation in patients treated for hemophilia.

Diabetes mellitus is a group of metabolic diseases in which a person has high blood sugar, either because the pancreas does not produce enough insulin, or because cells do not respond to the insulin that is produced. The treatment of diabetes concentrates on keeping blood sugar levels as close to normal ("euglycemia") as possible, without causing hypoglycemia. This can usually be accomplished with diet, exercise, and use of appropriate medications (insulin in the case of type 1 diabetes; oral medications, as well as possibly insulin, in type 2 diabetes).

Essential elements of the management of diabetes with insulin are periodic checks of the glucose concentration in the blood performed by the patients themselves, in order to obtain regular information on the progress and success of the prescribed treatment. This understanding, and patient participation is vital, since the complications of diabetes are far less common and less severe in patients who have well-managed blood sugar levels. With regard to this it has to be considered that the blood glucose level fluctuates throughout the day and is directly influenced by the amount of insulin administered, as well as lifestyle factors such as the amount and kind of food that is consumed, the exercise level and stress.

Therefore, the monitoring of the sugar level in the blood with a data management unit serves a dual purpose: on the one hand it provides the patient with information about the current status of glycemic control. On the other hand can the measured values serve as information for the patient or a healthcare professional (HCP) to determine whether an adjustment in the medication, namely the amount of insulin to be taken, is indicated.

In order to achieve these goals or to get as close as possible to the desired glycemic control, it is common practice that blood glucose measurement (BGM) values are monitored by a data management unit or a blood glucose meter comprising such data management unit once or several times during the day, following a testing regime normally prescribed by an HCP. Additionally, some data management units provide suggestions for doses of the medicament to be administered or for dose changes for example based on the present blood glucose value and ingested carbohydrates.

A special role is played by the so-called fasting blood glucose measurement value (FBG). A fasting blood glucose measurement value is derived after several hours without eating (6 to 8 hours). The fasting blood glucose measurement value is typically taken in the morning before breakfast and is the most commonly performed test among insulin treated patients as it is used to assess the quality of the titration of long-acting basal insulin or analogs such as insulin glargine.

In order to adjust or to adapt the therapy it is helpful to record the results of all blood glucose measurements and to analyze these results with the data management unit. Additionally, the administered doses and/or the ingested carbohydrates may be recorded. Therefore, typically a portable monitor is used which may be able to measure the blood glucose level as well or which receives the measurement values from a blood glucose measurement device. A wireless or wired data transfer can be used to transport the results from the measurement device to the data management unit. The administered doses or other data may be provided by the user input, for example using a keyboard.

In addition to the mere monitoring of the blood glucose level diabetic individuals often have to maintain tight control over their lifestyle so that they are not adversely effected by, for example, irregular food consumption or exercise. Further the HCP needs detailed information on the lifestyle of the patient to provide effective treatment or modification of treatment for controlling the disease. In former times, one of the ways of monitoring the lifestyle of a patient with diabetes has been for the individual to keep a paper logbook of their lifestyle. Currently, a number of portable electronic devices exists that can measure glucose levels in an individual and store the levels for recalling and uploading to another computer for analysis. Further, they provide functionality for storing lifestyle data for example by using a tag or flag associated to the individual measurement value.

Document EP 2 085 029 A1 refers to a method of operating an analyte measurement device having a display, user interface, processor, memory and user interface buttons. After measuring an analyte with the analyte measurement device the measurement value is displayed and the user is prompted to select a flag to associate the flag with the value. By pressing only one of the user interface buttons once the flag with the value of the device is stored. In particular, the user is prompted whenever a measuring step indicates that an analyte value is outside a predetermined range.

Document U.S. Pat. No. 7,570,980 B2 discloses blood glucose measurement data stored in an array comprising associated time code information for each measurement and various other flags. These flags may correspond to specific time frames, date information, calibration check information etc. From the measured and flagged values the so called effective meal average value is calculated encompassing the measurement values that occur at specific times, for example one hour before and one hour after a specified meal time.

As flags or tags are effective means in order to make the life of a diabetes patient easier they are nowadays widely used for data management. However, providing one measurement value with an associated tag or flag information is sometimes difficult for the patient. Further, it is important to make sure that the correct tag information is stored with the associated measurement value because if the information is confused the additional information which is provided with the tag to the measurement value is worthless.

Document WO 2011/007051 A1 discloses a method for controlling the measurement process of the blood glucose of a patient. Therein measurements are linked to events (such as meals) as pair measurements (pre-measurements and post-measurements) either fully automatically by pre-determined or adaptive time windows or fully manually by user assignment. The automatic assignment may be defective and does not allow overlapping of time windows. The manual assignment may also be defective and time consuming for the user as there are a high number of alternatives.

The computer-implemented diabetes management system described in US 2012/0266251 A1 allows the user to enter information pertaining to events (e.g. meals, exercise, periods of stress, etc.) by a menu selection that may affect the user's blood glucose measurement being read by the device. In particular, so-called acceptance time windows of varying lengths are defined during which blood glucose test values must be entered by the user for the blood glucose values to be included in a three day blood glucose test profile. The acceptance time windows are defined in different way, for example the preprandial acceptance time windows within two hours of the user typical breakfast, lunch and dinner meal times or the bedtime. The postprandial acceptance time windows may be set to begin ninety minutes after each of the actual breakfast, lunch and dinner times. A blood glucose test value fully automatically qualifies for inclusion in the three day test profile if only a single acceptance time window is open at this time and the acceptance window is one relating to a preprandial, postprandial, or bedtime acceptance time window. In case more than one acceptance time window is open at this time, the processing subsystem provides a query on the display asking the user to specify the label for the blood glucose value. The user manually selects the associated acceptance time window by touching the appropriate selection on the display. This procedure has the above mentioned drawbacks if the fully automatic assignment is executed. In the case of overlapping acceptance time windows it seems to be confusing for the user and hence error-prone as the user query and therefore also the user confirmation needed depends on the configuration of the time windows.

Aspects of the present invention may include a data management unit, a medical device and a respective method which makes it easier for the user to tag the data and to reduce the possibility for incorrect use of tags.

The above problem is solved by a data management unit with the features of claim 1.

In particular the inventive data management unit comprises
  a data storage adapted to store
    a plurality of measurement values of a physiological parameter, preferably a blood glucose level,
    for each measurement value an associated event tag,
    for each measurement value an associated time stamp,
    for at least two meal events an associated time range for tagging preselection, each time range is preferably user-settable,
    preferably also for a fasting event an associated time range for tagging preselection, this time range is preferably user-settable,
  a processor adapted to
    receive a new measurement value from the data storage or from a measurement unit, which is preferably at least shortly connected for data transfer,
    assign an associated time stamp to the new measurement value, if an associated time stamp does not yet exist with the new measurement value,
    receive selection data containing the information that the user has selected and/or confirmed either a "before meal" or an "after meal" tag with regard to the new measurement value,
    automatically select an additional associated tag referring to one of the at least two meal events and preferably also of the fasting event based on the selection data and on a comparison of the time stamp of the new measurement value with the associated time ranges for tagging preselection of the at least two meal events and preferably also with the time range for tagging preselection of the fasting event.

The time stamp associated to each measurement value comprises date and time information of a certain time point during the measurement process resulting in the respective measurement value, for example the completion of the measurement process or receipt of the new measurement value by the data management unit. Usually the time stamp is associated by the measurement unit and is transferred to the data management unit with the respective measurement value. In case the new measurement value is not associated with a respective time stamp by the measurement unit the time stamp is assigned by the processor after receipt of the measurement value.

With the event tag additional information associated with the measurement value is provided as explained above.

Preferably, the event tag for blood glucose measurement values comprises at least one of the events nil (no-tag) and in particular at least one of the following group of events comprising fasting, pre-meal breakfast, post-meal breakfast, pre-meal lunch, post-meal lunch, pre-meal supper, post-meal supper, night time and exercise, wherein the meal tags are composite tags as described below.

In one embodiment the data storage stores time ranges for tagging preselection for at least one meal event and for the fasting event and wherein the processor is adapted to automatically select the tag of one of the at least one meal event or the tag of the fasting event according to above comparison.

For example the following time ranges for tagging preselection may be defined:
  pre-meal breakfast: 5:00 a.m. to 8:59 a.m.
  fasting: 6:00 a.m. to 8:00 a.m.
  post-meal breakfast: 9:00 a.m. to 10:59 a.m.
  pre-meal lunch: 11:00 a.m. to 13:30 a.m.
  post-meal lunch: 12:00 p.m. to 3:59 p.m.
  pre-meal supper: 4:00 p.m. to 6:59 p.m.
  post-meal supper: 7:00 p.m. to 8:59 p.m.
  night time or bedtime: 9:00 p.m. to 11:59 p.m.
  exercise: 3:00 p.m. to 8:00 p.m.

At least part of the time ranges for tagging preselection may be set and changed by the user and/or HCP using for example the settings menu of the data management unit.

The time range for tagging preselection for the at least one predefined event refers to a time range which is used to support the user during tagging as follows. After receipt of a new measurement value of the physiological parameter and assignment of an associated time stamp, if necessary, the processor compares the time information of the associated time stamp with the time range for tagging preselection.

According to the invention the processor is adapted to automatically select the tag of one of the at least two meal events and preferably also of the fasting tag after one of the tags "before meal" or "after meal" was manually selected (and—if applicable also confirmed) by the user. By the manual selection and/or confirmation of the "before meal" or the "after meal" tag the so called selection data is generated (first component of the composite tag). This means that the "before meal" or the "after meal" tag was manually chosen and/or confirmed by the user. This includes the possibility that the "before meal" or the "after meal" tag is automatically suggested by the processor to the user but has to be manually confirmed by the user. Alternatively, the user choses and (thereby or additionally) confirms the "before meal" and "after meal" tag. Therefore the data storage may comprise the time ranges for tagging preselection of the meals, only, for example "breakfast", "lunch" and "dinner" or as indicated above. In particular, the time ranges for tagging preselection may overlap. Preferably, the "fasting" time range for tagging preselection is also provided. This embodiment also supports the user during tagging and reduces the risk of erroneous tagging. Additionally, the number of time ranges for tagging preselection may be reduced so that it is less time consuming to pre-set these time ranges and to choose the correct tag.

According to the invention the meal tag is a composite tag with a first component "before meal" or "after meal" and a second component referring to the particular meal or—if applicable—fasting. The processor selects the meal component of the tag automatically, preferably without user confirmation. In the latter case only a query for user input of the corresponding selection (i.e. a user confirmation and/or selection) of the first tag component "before meal" or "after meal" is provided. It is further possible for the user to change the automatically selected tag component or to select the no-tag.

In an alternative embodiment the fasting tag may be chosen in the first step in which the "before meal" or "after meal" tag can be selected as an alternative to these two tags. In this case, if the user choses the "fasting" tag instead of the "after meal" tag or the "before meal" tag, there is no automatic selection of a meal tag provided by the processor afterwards.

In an embodiment the time range for tagging preselection of a certain event may be different for working days and non-working days. In this case the determination whether the associated time stamp of the new measurement value is within the time range for tagging preselection is based not only on the time information of the time stamp but also on the date information.

Analogously, the above problem is also solved by a medical device comprising the above explained data management unit with the same advantages.

For the same reason the above problem is also solved by a method for operating a data management unit with a data storage comprising a preferably user-settable associated time ranges for tagging preselection for at least two meal events and preferably also a fasting event, wherein the method comprises the following steps:

receiving from the data storage or from a measurement unit, which is preferably at least shortly connected for data transfer, a new measurement value of a physiological parameter, for example a blood glucose level, assigning an associated time stamp to the new measurement value, if an associated time stamp does not yet exist with the new measurement value, receiving selection data containing the information that the user has selected and/or confirmed either a "before meal" or an "after meal" tag with regard to the new measurement value, automatically selecting an additional associated tag referring to one of the at least two meal events and preferably also of the fasting event based on the selection data and on a comparison of the time stamp of the new measurement value with the associated time ranges for tagging preselection of the at least two meal events and preferably also with the time range for tagging preselection of the fasting event.

During tagging a problem may arise if two measurement values refer to the same tag, for example to the fasting tag. As explained above the fasting blood glucose measurement value is particularly used to assess the quality of the titration of long-acting basal insulin or analogs. For the respective titration algorithm ("dose helper"), which gives the user a suggestion for a new basal insulin or analog dose or for a dose change, only one fasting blood glucose measurement value is considered.

Therefore, in an embodiment in case the tag referring to a particular first event, for example the fasting event, automatically selected for the new measurement value is already assigned to a previous measurement value for the same day, the processor is adapted to provide a user query whether the tag referring to the first event, e.g. the fasting event, is selected for the previous measurement value or for the new measurement value and the processor is further adapted to receive a data input by the user of a corresponding selection, i.e. a confirmation of the selection.

Alternatively, both, the previous measurement value and the new measurement value are associated to the fasting tag and during titration the user may be provided with a query as to which fasting value shall be used for the titration and preferably to confirm his/her selection by inputting the corresponding selection.

Additionally, in a further embodiment, in case no data input is received by the user (e.g. with regard to the selection whether the tag referring to the first event to the new measurement value or to the previous measurement value is selected as the one fasting value), for example because of a time-out of the data management unit, the processor is adapted to associate the tag to the previous measurement value or to the new measurement value according to a pre-defined selection rule or the nil tag.

For example, the rule defines that the tag is associated to the fasting value which falls within the time range for fasting tag preselection, and, if both values fall within this time range, the tag is associated to the one which has the younger time stamp or to the fasting value which is higher. Similarly, the rules may be defined with regard to the selection of one fasting value within the titration.

In a further embodiment the processor is further adapted to receive a data input from the user related to the physiological parameter, wherein the data input comprises at least one of the following parameters:

occurrence or number of hypoglycemic events after a predetermined point in time, e.g. a last use of the medical device or the time stamp of the last (previous) measurement value, occurrence or number of hyperglycemic events after a predetermined point in time, e.g. the last use of the medical device or the time stamp of the last (previous) measurement value, size of the injected medicament dose after a predetermined point in time, e.g. the last use of the medical device or the time stamp of the last (previous) measurement value, wherein preferably the injected medicament dose is automatically selected as the dose of the last (previous) suggested dose.

The above mentioned data input may be facilitated after tagging or during titration.

These additional parameters may be used for further calculations, data display, for the assessment of the disease or for the titration algorithm. Additionally, the preselection of the dose as the last suggested dose reduces the risk for erroneous dose data.

For the same reason as explained above the problem is solved by a computer program for operating a data management unit with a data storage comprising a preferably user-settable associated time ranges for tagging preselection for at least two meal events and preferably also a fasting event, wherein the method comprises the following steps:
- code for receiving a new measurement value of a physiological parameter, for example a blood glucose level, from the data storage or from a measurement unit, which is preferably at least shortly connected for data transfer,
- code for assigning an associated time stamp to the new measurement value, if an associated time stamp does not yet exist with the new measurement value,
- receiving selection data containing the information that the user has selected and/or confirmed either a "before meal" or an "after meal" tag with regard to the new measurement value,
- code for automatically selecting an additional associated tag referring to one of the at least two meal events and preferably also of the fasting event based on the selection data and on a comparison of the time stamp of the new measurement value with the associated time ranges for tagging preselection of the at least two meal events and preferably also with the time range for tagging preselection of the fasting event.

The above computer program may be realized with the embodiments as mentioned above with regard to the above inventive method for operating a medical device.

The above problem is further solved by computer program product comprising a computer-readable medium bearing computer program code embodied therein for use with a computer, wherein the computer program code comprises the above mentioned computer program.

The above-mentioned advantages as well as other advantages of various aspects of the present invention will become apparent to those of ordinary skill in the art by reading the following detailed description with the explanation of the accompanying drawings. All features described above and below and/or illustrated per se or in any combination form the subject-matter of the invention, independent of their inclusion in the claims or their back-reference.

Exemplary embodiments of the present invention are described herein with reference to schematic drawings, in which.

The following paragraphs will describe various embodiments of the invention. For exemplary purpose only, the embodiments are outlined in relation to a medical device with regard to blood glucose level measurement. However, the used terminology and the description of the embodiments with respect to the medical device or the method are not intended to limit the principles and ideas of the invention to such a single device or method and may be adapted to other physiological values accordingly.

Figure 1:
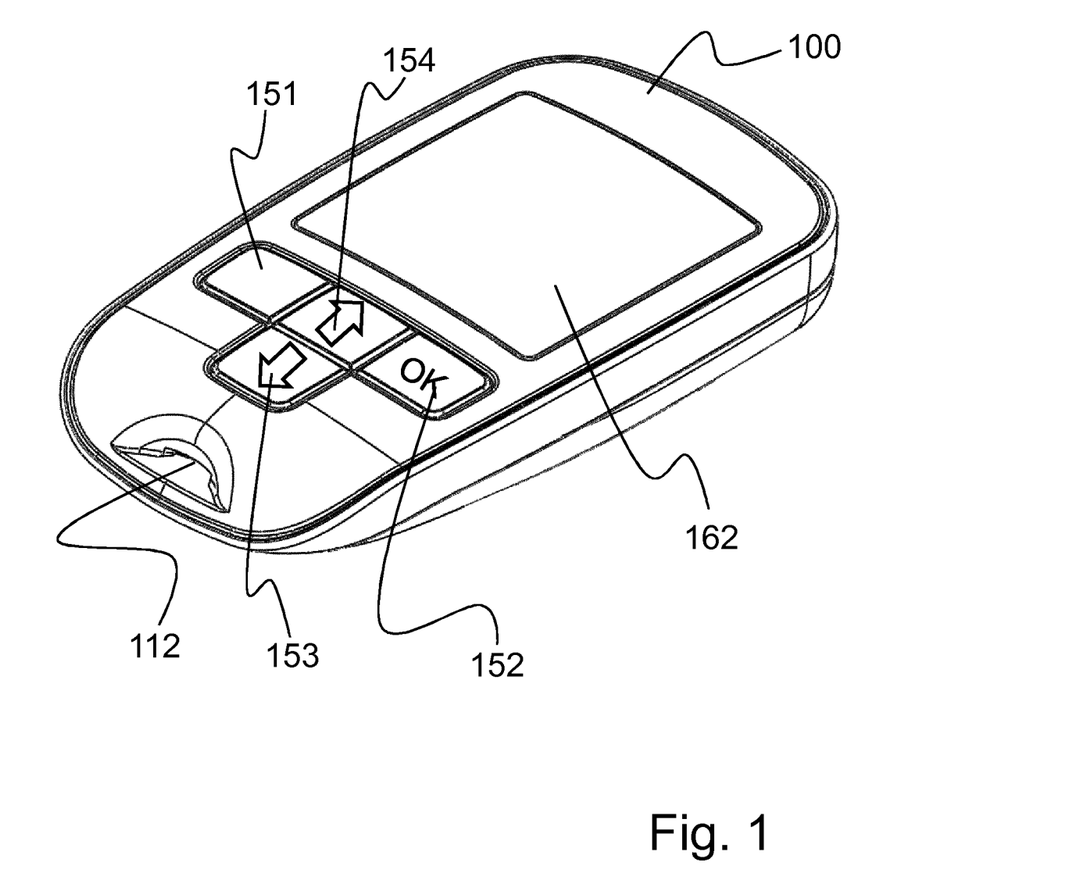
FIG. 1 shows the medical device according to a preferred embodiment of the invention in a perspective view.
Figure 2:
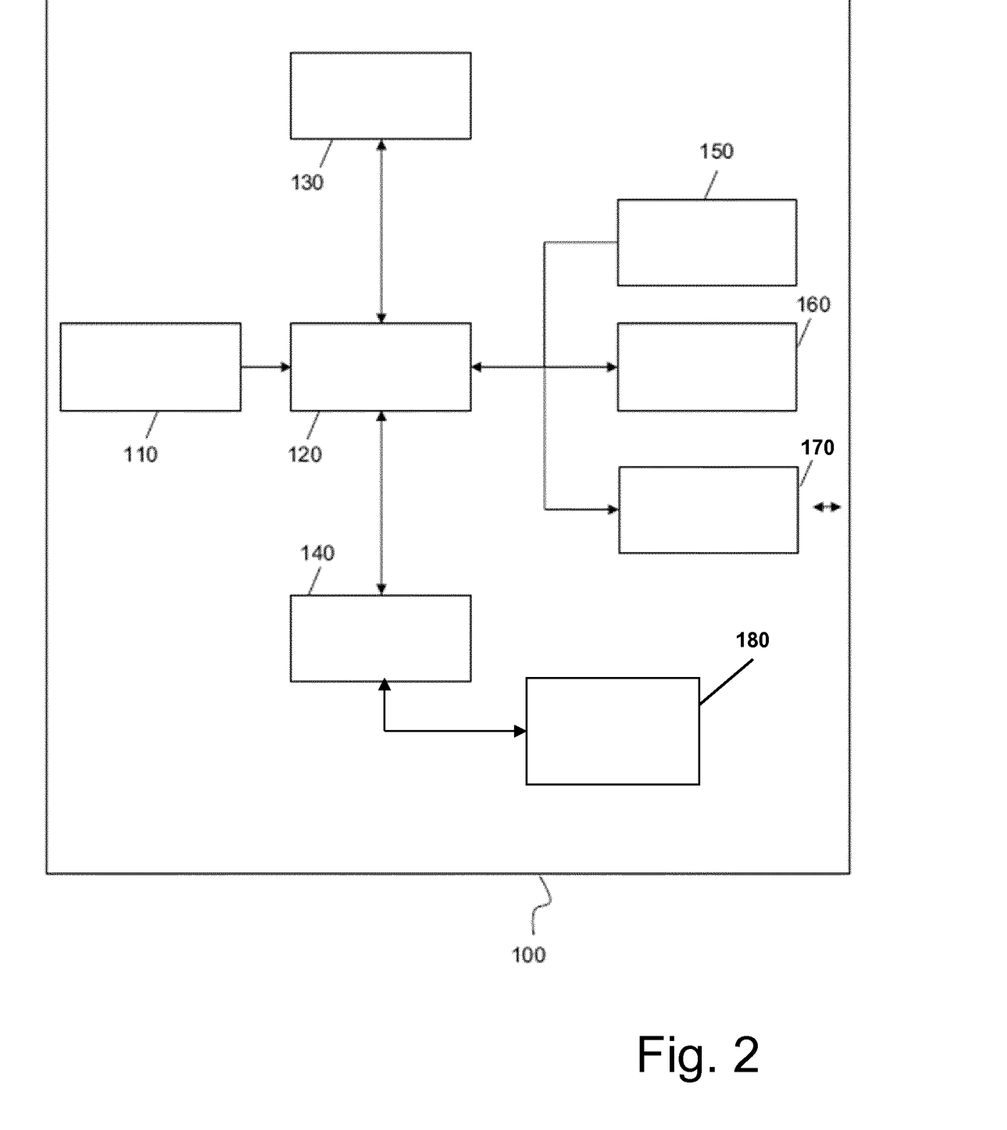
FIG. 2 shows a diagram of the medical device as shown in FIG. 1.

FIG. 1 is a schematic drawing and FIG. 2 is a schematic diagram of the medical device 100 according to a preferred embodiment of the invention. Preferably, the medical device 100 comprises a blood glucose measurement unit 110, which is arranged to measure the blood glucose level. Further, the measurement unit 110 comprises an interface and a slot 112 for inserting a test strip.

The blood glucose measurement unit 110 is connected to a receiving unit 120, which is arranged to forward e.g. blood glucose measurement data received from blood glucose measurement unit 110 to a data storage 130 (storage unit or means) or memory, such as a Flash memory. Alternatively, the receiving unit 120 may retrieve stored data such as e.g. blood glucose value data from the storage 130 and forward it to a processor 140 (processing unit or means), such as a microcontroller or microprocessor, a digital signal processor, and/or the like. Alternatively, the receiving unit 120 directly forwards the blood glucose value data received from the blood glucose measurement unit 110 to the processor 140.

Receiving unit 120 is further connected to a user input unit 150 of a user interface. The user input unit 150 is arranged to receive input from the user of the medical device 100 for example by key 151, confirmation key (OK button) 152, key 153 for scrolling down (downward button) and key 154 for scrolling up (upward button). The user input data are forwarded from the user input unit 150 to the receiving unit 120, which either forwards it to the processor 140 or to the data storage 130.

Furthermore, the user interface of medical device 100 comprises a display unit 160 with a display 162, which is connected to the receiving unit 120 as well. Preferably, the display unit 160 receives data to be displayed by the display 162 from the receiving unit 120 or the processor 140.

Preferably, the medical device 100 additionally comprises a further interface 170, for example a wired interface such as a serial port, a Universal Serial Bus (USB) interface, a mini-USB interface, or a wireless interface such as an infrared (e.g. an IRDA) interface, a Bluetooth™ interface, and/or the like, in order to receive data and/or to transmit data. The interface 170 is preferably connected to the receiving unit 120 in order to receive data from the receiving unit 120 and/or to forward data to the receiving unit 120.

Additionally, the medical device 100 comprises a clock unit 180 which provides a date and time information, preferably based on a clock generator, which may be displayed at the display 162. Further, the clock unit 180 provides date and time information in particular for generating a time stamp for an associated blood glucose measurement.

As outlined above, the medical device 100 preferably comprises a blood glucose measurement unit 110. Preferably, the blood glucose measurement unit 110 is arranged to measure the blood glucose level in the blood of e.g. the user by testing a drop of blood on a test strip that is inserted into the slot 112. The measurement may be conducted using e.g. an electrochemical method. Full insertion of the test strip in the slot 112 may be detected by a respective sensor. The measured blood glucose value is transformed to blood glucose value data and forwarded preferably immediately or on demand to the receiving unit 120. Alternatively, the blood glucose measurement unit 110 is arranged to measure the blood glucose level of the user via infrared diagnosis or an alternative contactless measurement method.

According to a further alternative (not depicted in FIG. 1) the blood glucose measurement unit 110 is implanted in the body of the user of the medical device and forwards the data to the receiving unit 120 either via a wired connection or via a wireless connection. In an embodiment, such an implanted blood glucose measurement unit 110 is a continuous measurement sensor e.g. based on a chip which may allow a continuous closed loop control. In the latter case the medical device comprises two parts, one part contains the measurement unit 110 and the other part the remaining units of the medical device. The blood glucose measurement unit 110 preferably forwards the blood glucose measurement value data to the receiving unit 120 via interface 170. According to a further alternative the medical device does not comprise a blood glucose measurement unit which measures the blood glucose values, but receives blood glucose value data from an external unit.

The measurement of the blood glucose measurement is preferably triggered by the receiving unit 120 which sends a respective signal to the blood glucose measurement unit 110. According to one preferred alternative the receiving unit 120 receives a trigger signal generated by user input which is received via user input unit 150 or based on a signal from the slot 112 detecting a test strip. Alternatively, the trigger signal is generated automatically by the clock unit 180 or by the processor 140.

Preferably, the receiving unit 120 is represented e.g. by the input ports and output ports of a microprocessor or a bus system managing the data handling between several functional units. This includes bus systems, such as e.g. Advanced Microprocessor Bus Architecture bus systems implemented in a microprocessor or external bus systems connected to a microprocessor. Via the receiving unit 120, data are retrieved from the data storage 130 on demand and forwarded to the processor 140, to the display unit 160 or to the interface 170. Moreover, the receiving unit 120 forwards control signals, such as trigger signals or control signals e.g. to the blood glucose measurement unit 110, the display unit 160 or the interface 170.

The data storage 130 is arranged to store data entered via the user input unit 150, a plurality of blood glucose measurement data received from the blood glucose measurement unit 110 together with the time stamp and/or at least one event tag associated to each measurement data, data calculated from the plurality of blood glucose measurement values processed by the processor 140 and/or data received via interface 170.

Further the data storage 130 stores parameter data like an associated time range for tagging preselection regarding for example a fasting tag. Preferably such a time range is defined using a center time and a duration, wherein the time range comprises the time around the center time with the size of ½ duration in both directions. For example, the time range for fasting tag preselection is defined with a duration of 2 hours and a center time at 7 a.m., so that the time range for fasting tagging preselection encompasses the time between 6 a.m. and 8 a.m.

Additionally, for example the data storage 130 stores the following preset time ranges for pre- and post-meal times for tagging preselection:
  pre-meal breakfast: 5:00 a.m. to 8:59 a.m.
  post-meal breakfast: 9:00 a.m. to 10:59 a.m.
  pre-meal lunch: 11:00 a.m. to 13:30 a.m.
  post-meal lunch: 12:00 p.m. to 3:59 p.m.
  pre-meal supper: 4:00 p.m. to 6:59 p.m.
  post-meal supper: 7:00 p.m. to 8:59 p.m.
  night time or bedtime: 9:00 p.m. to 11:59 p.m.

Mealtime and fasting time ranges may be settable by the user "Settings" mode of the medical device. The above meal tags are composite tags with the first component "pre-meal" or "post-meal" and the second component regarding the meal type, namely "breakfast", "lunch" or "supper".

Alternatively, the data storage 130 stores the following user-settable time ranges for tagging preselection with regard to meal times:
  breakfast: 5:00 a.m. to 10:59 a.m.
  lunch: 10:30 a.m. to 3:59 p.m.
  supper: 4:00 p.m. to 8:59 p.m.

Furthermore, data storage 130 is arranged to provide the stored data to the processor 140, to the display unit 160 and/or to the interface 170. The data storage 130 is preferably implemented as a semiconductor memory such as a Flash memory. Alternatively, it is implemented as a hard disk memory or an on-chip memory of the processor 140.

The processor 140 is preferably a microprocessor or any other functional unit capable of processing data.

The user input unit 150 is preferably implemented as a keyboard comprising one or more push buttons 151, 152, 153, 154. The keyboard may comprise one or more soft keys, wherein the function of the soft keys may be displayed on the display 162. Alternatively, the user input unit 150 is a key board or a touch screen. Alternatively, the user input unit 150 comprises a microphone for receiving speech input so that data can be entered via speech input.

After facilitating a blood glucose measurement a tag may be automatically associated to the measurement value referring to lifestyle data as explained below in detail. The automatically selected tag may be changed by pressing the up or down keys 153, 154 scrolling upwards or downwards through the different tags which are for example the fasting tag, pre-meal tag, post-meal tag and no-tag, respectively, referring to a measurement value which is a fasting blood glucose value, a pre-meal blood glucose value, a post-meal blood glucose value and a blood glucose value that cannot be associated to one of the previous lifestyle parameter.

The display unit 160 preferably comprises an LCD or LED display 162. Preferably, the display displays a number of alphanumerical characters so that e.g. the presently measured blood glucose value can be displayed together with additional instructions for the user. Alternatively or additionally, the display unit 160 comprises a graphic display in order to display graphs or graphics such as icons. Further the display of the display unit 160 may comprise a touchscreen.

The interface 170 is preferably a wireless interface, such as IRDA, Bluetooth™, GSM, UMTS, ZigBee, or WI-FI, etc. Alternatively, the interface is a wired interface, such as a USB port, mini-USB port, serial data port, parallel data port, etc., for receiving and transmitting data. In a further alternative embodiment the medical device 100 does not comprise an interface 170.

According to another alternative embodiment, medical device 100 comprises a memory card reader or a memory card reader interface. The memory card reader is preferably adapted to read information from a memory card, such as a Flash memory card, or any type of SIM card. For this purpose, the memory card comprises a memory, wherein at least one of a selected algorithms together with corresponding parameters, a history of the blood glucose values and/or insulin doses administered, etc. is stored. Thus, in the case that the medical device 100 has a defect, the relevant data may still be stored on the memory card which can be easily removed from the memory card reader of the medical device 100 and transferred to a new medical device 100. Moreover, the memory card 100 may be used in order to provide information on the history of the treatment to e.g. an HCP.

In the case that the memory card is a SIM card providing subscriber identification for a mobile communication network and the interface unit 170 is additionally a mobile communication interface, additional functions of the medical device 100 can be unlocked by the provider of the SIM card via a telecommunication channel. This offers the possibility that the medical device 100 can communicate with other telecommunication devices via predefined channels, such as UMTS or GSM. Via the international mobile subscriber identity, also called IMSI, stored in the SIM card, the medical device 100 identifies itself within the network and, thus, can be addressed via the network. In such a case the medical device 100 can be easily checked, remote controlled, updated, monitored, etc., via interface unit 170, e.g. by addressing the mobile communication unit with a phone number.

Furthermore, the medical device 100 is able to transmit data via SMS, e-mail or via mobile internet connection. Moreover, this offers the possibility to locate the medical device 100 in an emergency case.

In the case that the blood glucose measurement unit 110 is a sensor which is e.g. implanted a dose delivery unit with an insulin pump forming an automatic delivery system may be additionally provided.

Figure 5:
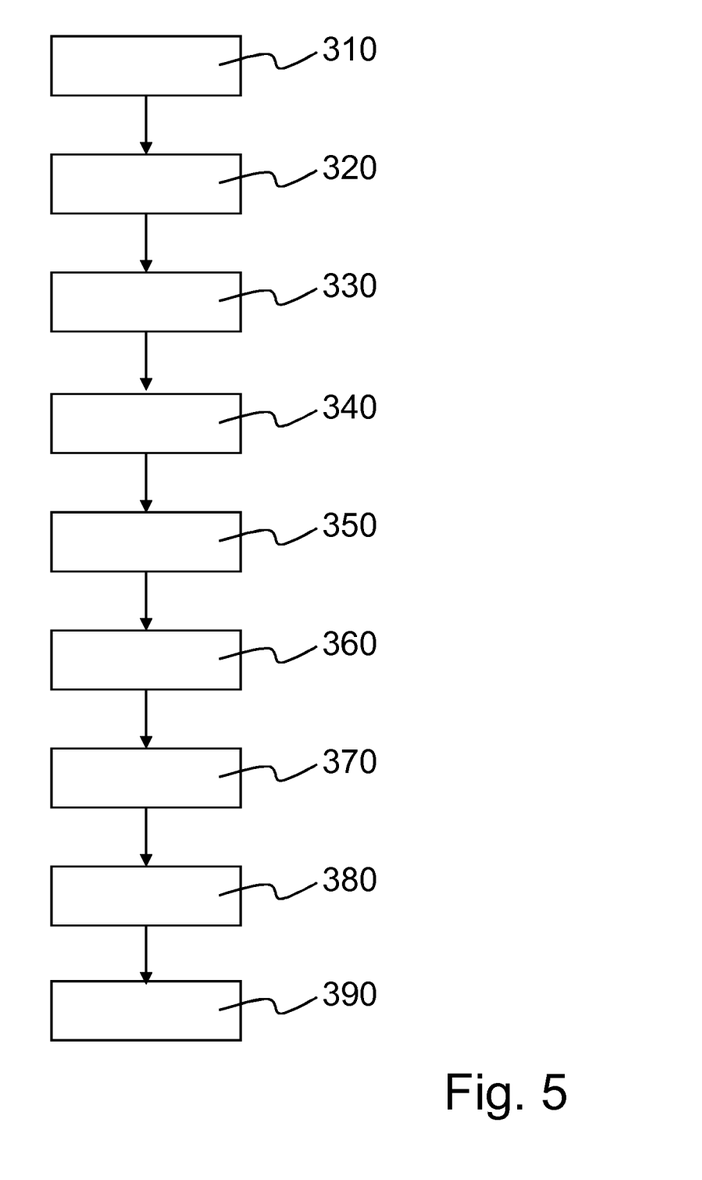
FIG. 5 a flow diagram comprising the inventive method realized by the inventive medical device in the "Measure BG" mode.

As shown in FIG. 5, the medical device 100 is capable to perform a number of process steps. According to one embodiment after switching on, e.g. by pressing a key 151, 152, 153 or 154, preferably the confirmation key 152 for a predetermined time, or detection of a test strip within the slot 112, the medical device 100 performs initialization step 310 for initializing the functional components of the medical device 100. After this, the different operation modes which are implemented in the medical device 100, are displayed in the display step 320, preferably operation modes such as "Measure BG", "Logbook", "Settings" and/or "Titration".

In step 330 the user selects one of the displayed operation modes via the user input unit 150, for example by means of the keys 153, 154 for scrolling down or up, and confirms the selection using the confirmation key 152.

In step 340 the selected operation mode is executed. As an example the mode "Measure BG" is selected for executing a blood glucose measurement. Upon execution of this mode the user/patient is requested to provide a test strip with a blood sample.

In the "Logbook" mode the history of previous measurements and statistical results may be calculated and displayed. The "Settings" mode allows the user to define and change some parameters of the medical device 100, e.g. time ranges for tagging preselection for a number of pre-set events. In the "Titration" mode a dose suggestion may be provided by the medical device 10 for basal insulin or analogue.

After selecting the mode "Measure BG", in step 350 a drop of blood is applied to the test portion of the test strip which is inserted in slot 112 of the medical device 100.

According to an alternative version of the operation process steps 310 to 340 may be skipped in the case that a specific operation mode is preselected. In this case, after initialization, the preselected operation mode, which is either preselected by the user or automatically selected in accordance with a specific event, for example the detection of a fully inserted test strip in slot 112, the operating process proceeds with the following step 350 and asks the user to apply a drop of blood. In step 360 it executes the preselected one or more operation modes, for example the mode "Measure BG".

Now in step 360 the measurement unit 110 determines e.g. by an electrochemical or an optical method the blood glucose level and displays the respective new measurement value at the display 162.

In the next step 370 the clock unit 180 generates a time stamp of the present measurement comprising a date and time information. The time stamp is also displayed in display 162 and both, the present blood glucose measurement value and the associated time stamp is transferred by receiving unit 120 to the data storage 130.

Figure 4:
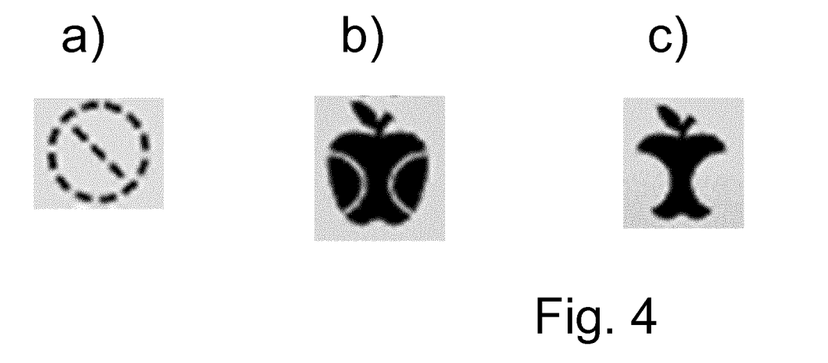
FIG. 4 further examples of tag signs as they are displayed on a display of the medical device as shown in FIG. 1.

In the next step 380, the user manually selects one of the event tags "pre-meal" and "post-meal" represented by a full apple as shown in FIG. 4b) in case of the pre-meal tag and represented by a bitten apple as shown in FIG. 4c) in case of the post-meal tag and confirms the tag. Thereby, the processor 140 may provide a suggestion with regard to the "pre-meal" or "post-meal" tag which is to be manually confirmed by the user. Then, the processor 140 automatically selects the associated meal according to the above time range for meal times according to the time information of the time stamp, preferably without further user confirmation. This could be decided e.g. by the fact whether the time stamp lies within the first half (pre-meal) or the second half (post meal) of the respective time window. For example, the processor selects "breakfast" if the time information of the present time stamp is 10:45 a.m. and the user has confirmed the "post-meal" tag or it selects "lunch" if the user has confirmed the "pre-meal" tag. Accordingly, the tag comprises the information "pre-meal" or "post-meal" and "breakfast" or "lunch" and forms a respective composite tag which is then stored in the data storage 130 initiated by the processor 140 via the receiving unit 120.

In order to show that a confirmation is necessary the tag sign 168 displayed on display 162 is blinking/flashing. Now, the user may confirm the fasting tag for example by pressing the confirmation key 152. Alternatively, the user may change the tag using the up and down keys 153, 154 into the pre-meal tag, the post-meal tag or the no-tag (nil). If the correct tag is chosen the user confirms the tag by pressing the confirmation key 152. By confirmation of the tag with the confirmation key 152 the flashing of the displayed tag sign is stopped and the tag sign is displayed continuously without blinking. In this state, pressing the up/down keys 153, 154 will not change the tag.

If in step 380 the processor 140 cannot find any range for tagging pre-selection which refers to the time information of the time stamp of the present measurement value, the no-tag may be automatically selected.

After pressing the confirmation key 152, if the user presses the confirmation key again, the tag will start flashing again and pressing the up/down key will again allow the user to change the tag as explained above.

Further, in the "Logbook" mode the user is allowed to change the tag in the above explained manner but only within a predefined time range from the associated time stamp of the blood glucose measurement value, for example within 10 days.

If the time stamp of the recent measurement value falls within the current time range for fasting tagging pre-selection and there is already a measurement value of that day marked as fasting the user is asked which measurement value shall be associated to the fasting tag. After selection of one of the measurement values as the fasting value the selection is confirmed by the user.

Further, if, for example the fasting time range for tagging preselection overlaps with, for example the time range for (pre-meal) breakfast, the fasting tag has priority over the (pre-meal) breakfast tag. Hence, in this case, if no fasting value is recorded for that day, the fasting tag is automatically selected if the time stamp of the present measurement value lies within the time range for the fasting tag and the time range for pre-meal breakfast.

In another embodiment a flashing tag may not only be confirmed by the user by pressing the confirmation key 152 but also by removal of the strip from the port 112 after a blood glucose test, or when the medical device goes into sleep mode.

In the next optional step 390 a comment to the present measurement value may be selected by the user using the up and down keys 153, 154. The comment may then be confirmed with the confirmation key 152, wherein the chosen comment is then stored in the data storage 130 associated to the present measurement value as well.

Alternatively or additionally, the user may be asked in step 390 whether there are hypoglycemic events (hypos) are occurred and, if yes, which number, and/or whether there are hyperglycemic events (hypers) are occurred and, if yes, which number, since last measurement or last use of the medical device 100. Alternatively or additionally the user has to provide the information about the size of the injected medicament dose after a predetermined point in time, e.g. last use of the medical device or the time stamp of the last (previous) measurement value, wherein preferably the injected medicament dose is automatically selected as the dose of the last (previous) suggested dose by a titration method.

When the medical device 100 is in the "Measure BG" mode, the device may turn into the sleep state automatically after for example 120 seconds without any new action. Once the device has returned a new measurement value, the device turns to the sleep state automatically after for example 60 seconds without any user interaction.

As explained above the medical device 100 provides at least one memory review mode which is called "Logbook" mode. The respective display and calculations are explained in the following.

The "Logbook" mode is entered when the user activates the medical device 100 by pressing e.g. the confirmation button 152. Then a display as depicted in FIG. 3 is shown.

In the "Logbook" the measurement values are preferably displayed in the order in which the entries are entered into the device, or alternatively according to the time and date assigned to the measurement values. In particular the most recent blood glucose measurement value is shown upon entry into the "Logbook" mode. Pressing the up and down keys 153, 154 the user may scroll through the records, for example by pressing the down key 153 the user may scroll backwards in time and by pressing the up key 154 the user scrolls forward in time.

Figure 3:
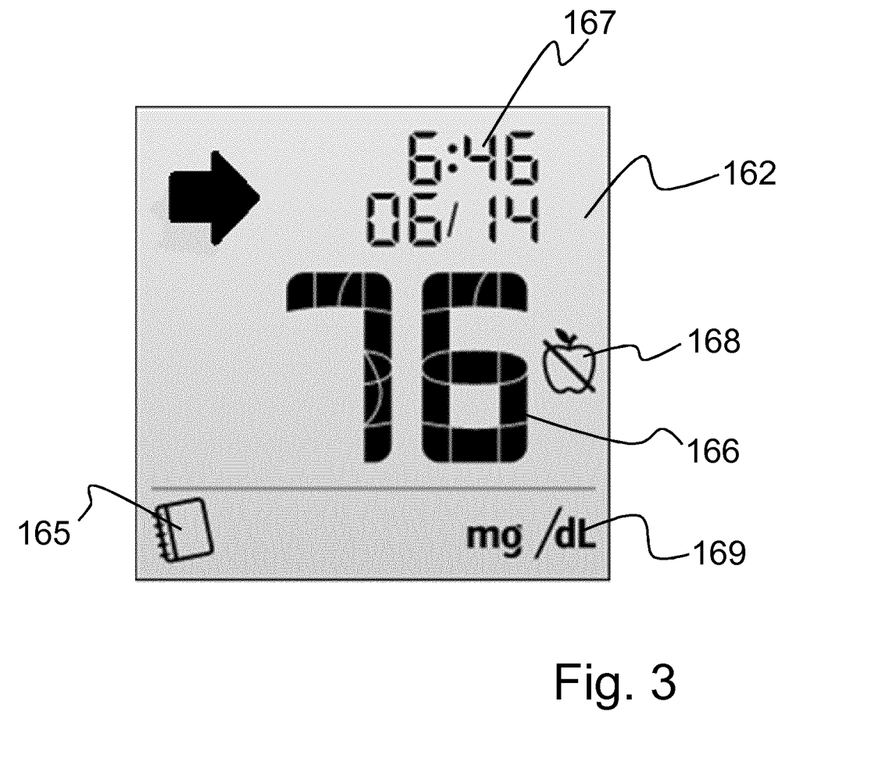
FIG. 3 an example of the display of the medical device as shown in FIG. 1 in a "Logbook" mode.

One Example of a display 162 showing a measurement value is depicted in FIG. 3. The user knows from the "Book" sign 165 in the lower left corner of the display that he/she has entered the "Logbook" mode.

The display 162 in the "Logbook" mode further shows the blood glucose measurement value 166 as biggest number in the center of the screen. Above the measurement value 166 the associated time stamp 167 including date and time is displayed. On the right side the associated tag as a sign 168 is provided, wherein the sign may show for example an empty, struck out apple as shown in FIG. 3 in case of an associated fasting tag, a full apple as shown in FIG. 4b) in case of an associated pre-meal tag, a bitten apple as shown in FIG. 4c) in case of an associated post-meal tag or a struck out circle as shown in FIG. 4a) in case of an associated no-tag. Additionally, in the lower right corner of the display 162 the measurement unit 169 for the blood glucose value is provided.

In the "Titration" or "Dose Helper" mode the user is provided with a dose suggestion preferably for basal insulin or analog if some of predefined conditions are fulfilled. The method used in this mode is based on at least the most recent fasting glucose value and other information like number of hypers and hypos and/or previous doses. Hence, in this mode the user is asked, in case there are two fasting measurement values within one single day tagged with the fasting tag, which fasting blood glucose measurement value has to be used for the titration algorithm. Further, additional data are requested from the user like occurrence or number of hypoglycemic events after a predetermined point in time, e.g. a last use of the medical device or the time stamp of the last (previous) measurement value, occurrence or number of hyperglycemic events after a predetermined point in time, e.g. the last use of the medical device or the time stamp of the last (previous) measurement value, size of the injected medicament dose after a predetermined point in time, e.g. the last use of the medical device or the time stamp of the last (previous) measurement value, wherein preferably the injected medicament dose is automatically selected as the dose of the last (previous) suggested dose.

From these data the "Dose Helper" determines whether the actual dose must be changed and provides the user with a proposal of a dose change or of a new dose, if applicable.

As explained above in an example embodiment, device 100 may be realized as a two-part device, wherein the data storage 130, the receiving unit 120, the processor 140, the user input unit 150, the display unit 160 with the trend indicator 164, the interface unit 170, and the clock unit 180 are realized in a device like a smartphone or another computer separate from the measurement unit 110. The inventive method runs as a software program (application or "app") on the hardware of the device. The keys 151, 152, 153 and 154 are realized in this case as button fields on the display of a touchscreen.

The invention claimed is:

1. A blood glucose measuring system, comprising:
a blood glucose measuring unit configured to generate blood glucose measurement values of blood samples, the blood glucose measuring unit comprising a slot for receiving the blood samples;
a user interface comprising a display device; and
an apparatus communicatively coupled to the blood glucose measurement unit, the apparatus comprising:
a data storage adapted to store:
a plurality of blood glucose measurement values generated by the blood glucose measurement unit,
for each blood glucose measurement value an associated event tag,
for each blood glucose measurement value an associated time stamp,
an associated time range for tagging preselection for each of at least two meal events, and
a processor adapted to:
receive a new blood glucose measurement value from the data storage or from the blood glucose measurement unit, assign an associated time stamp to the new blood glucose measurement value using a clock unit, if an associated time stamp does not yet exist with the new blood glucose measurement value, cause display, on the display device of the user interface, of one or more first graphical representations prompting a user of the blood glucose measurement system to select and/or confirm one of a "before meal" tag and an "after meal" tag with regard to the new blood glucose measurement value;

receive selection data from the user interface containing information that the user of the blood glucose measurement system has selected and/or confirmed one of a "before meal" tag and an "after meal" tag with regard to the new blood glucose measurement value, automatically determine an additional associated meal event tag referring to the one of the at least two meal events based at least partially on the received selection data and a comparison of the time stamp of the new blood glucose measurement value with the associated time ranges for tagging preselection of the at least two meal events stored in the data storage, store, in the data storage, each new blood glucose measurement value, its associated time stamp, its associated "before meal" tag or "after meal" tag, and its associated meal event tag;

determine a medicament dose suggestion based on the stored blood glucose measurement values, its associated "before meal" and "after meal" tag, and its associated meal event tag; and cause display, on the display device of the user interface, of one or more second graphical representations indicating the determined medicament dose suggestion to be used to adjust a medication.

2. The blood glucose measurement system according to claim 1, wherein if the automatically determined additional associated meal event tag is already assigned to a previous blood glucose measurement value of the same day, the processor is adapted to provide a user query whether the automatically selected additional associated meal event tag is selected for the previous blood glucose measurement value or for the new blood glucose measurement value and the processor is further adapted to receive a user input of a corresponding selection.

3. The blood glucose measurement system according to claim 2, wherein in case no selection data is received, the processor is adapted to associate the automatically determined additional associated meal event tag to the previous blood glucose measurement value or to the new blood glucose measurement value according to a pre-defined selection rule.

4. The blood glucose measurement system according to claim 1, wherein the selected and/or confirmed one of a before meal tag and after meal tag comprises at least one of the event nil, fasting, pre-meal breakfast, post-meal breakfast, pre-meal lunch, post-meal lunch, pre-meal supper, post-meal supper, night time and exercise.

5. The blood glucose measurement system according to claim 1, wherein the processor is further adapted to receive a data input related to the blood glucose measurement value, wherein the data input comprises at least one of the following parameters:

occurrence or number of hypoglycemic events after a predetermined point in time, occurrence or number of hyperglycemic events after a predetermined point in time, and size of an injected medicament dose after a predetermined point in time.

6. The blood glucose measurement system according to claim 1, wherein, each time range is user-settable.

7. The blood glucose measurement system according to claim 1, wherein the data storage is configured to store an associated time range for tagging preselection for a fasting event, and wherein the processor is adapted to automatically determine an additional associated meal event tag referring to the one of the at least two meal events and also of the fasting event based on the selection data and on to a comparison of the time stamp of the new blood glucose measurement value with the associated time ranges for tagging preselection of the at least two meal events and also with the time range for tagging preselection of the fasting event.

8. The blood glucose system according to claim 5, wherein the injected medicament dose is automatically selected as the dose of the last suggested dose.

9. A method for operating a blood glucose measurement system with a data storage comprising associated time ranges for tagging preselection for at least two meal events, wherein the method comprises the following steps:

receiving a new blood glucose measurement value from the data storage or from a blood glucose measurement unit of the blood glucose measurement system, assigning, using a clock unit, an associated time stamp to the new blood glucose measurement value, if an associated time stamp does not yet exist with the new blood glucose measurement value, causing display, on a display device of a user interface of the blood glucose measurement system device, of one or more first graphical representations prompting a user of the blood glucose measurement system to select and/or confirm one of a "before meal" tag and an "after meal" tag with regard to the new blood glucose measurement value;

receiving selection data containing information that the user of the blood glucose measurement system has selected and/or confirmed one of a "before meal" tag and an "after meal" tag with regard to the new blood glucose measurement value, automatically determining an additional associated meal event tag referring to one of the at least two meal events based at least partially on the received selection data and on a comparison of the time stamp of the new blood glucose measurement value with the associated time ranges for tagging preselection of the at least two meal events stored in the data storage, storing, in the data storage, each new blood glucose measurement value, its associated time stamp, its associated "before meal" tag or "after meal" tag and its associated meal event tag, determining a medicament dose suggestion based on each of the stored blood glucose measurement values, its associated "before meal" and "after meal" tag, its associated meal event tag, and causing display, on the display device of the user interface, of one or more second graphical representations indicating the determined medicament dose suggestion; and using the displayed medicament dose suggestion to adjust a medication.

10. The method according to claim 9, further comprising the step:

if the automatically determined additional associated meal event tag is already assigned to a previous blood glucose measurement value of the same day, displaying, on the user interface, a user query whether the automatically selected an additional associated meal event tag is selected for the previous blood glucose measurement value or for the new blood glucose measurement value, and receiving, from the user interface, a user input of a corresponding selection.

11. The method according to claim 10, wherein in case no user input is received, associating the automatically determined additional associated meal event tag to the previous blood glucose measurement value or to the new blood glucose measurement value according to a pre-defined selection rule.

12. The method according to claim 9, wherein the meal event tag comprises the event nil and at least one of the following group of events comprising fasting, pre-meal breakfast, post-meal breakfast, pre-meal lunch, post-meal lunch, pre meal supper, post meal supper, night time and exercise.

13. The method according to claim 9, further comprising:
receiving, from the user interface, a data input related to the blood glucose measurement value, wherein the data input comprises at least one of the following parameters:
occurrence or number of hypoglycemic events after a predetermined point in time,
occurrence or number of hyperglycemic events after a predetermined point in time, and
size of an injected medicament dose after a predetermined point in time.

14. The method according to claim 13, wherein the injected medicament dose is automatically selected as the dose of the last suggested dose.

15. A computer program product comprising a non-transitory computer-readable medium bearing computer program code embodied therein for use with a computer, wherein the computer program code comprises:
instructions for operating an apparatus of a blood glucose measurement system, the apparatus comprising a data storage comprising associated time ranges for tagging preselection for at least two meal events,
instructions for receiving a new blood glucose measurement value from the data storage or from a blood glucose measurement unit of the blood glucose system, the blood glucose measurement unit configured to generate blood glucose measurement values based on a blood sample received at a slot of the blood glucose measurement unit,
instructions for assigning, using a clock unit, an associated time stamp to the new blood glucose measurement value, if an associated time stamp does not yet exist with the new blood glucose measurement value,
instructions for causing display, on a display device of a user interface of the blood glucose measurement system, of one or more first graphical representations prompting a user of the blood glucose measurement system to select and/or confirm one of a "before meal" tag and an "after meal" tag with regard to the new blood glucose measurement value
instructions for receiving selection data containing information that the user of the blood glucose measurement system has selected and/or confirmed one of a "before meal" and an "after meal" tag with regard to the new blood glucose measurement value,
instructions for automatically determining an additional associated meal event tag referring to one of the at least two meal events based on the selection data and on a comparison of the time stamp of the new blood glucose measurement value with the associated time ranges for tagging preselection of the at least two meal events stored in the data storage,
instructions for storing, in the data storage, each new blood glucose measurement value, its associated time stamp, its associated "before meal" tag or "after meal" tag and its associated meal event tag, and
instructions for determining a medicament dose suggestion based on each of the stored blood glucose measurement values, its associated "before meal" and "after meal" tag, its associated meal event tag, wherein the medicament dose suggestion is to be used to adjust a medication: and
instructions for causing display, on the display device, of one or more second graphical representations indicating the determined medicament dose suggestions to be used to adjust a medication.

16. The computer program according to claim 15, further including instructions for automatically determining an additional associated meal event tag referring to one of the at least two meal events and the fasting event based on the selection data and on a comparison of the time stamp of the new blood glucose measurement value with the associated time ranges for tagging preselection of the at least two meal events and with the time range for tagging preselection of the fasting event.

17. The computer program according to claim 15, wherein, each time range is user-settable.

18. A blood glucose measurement system, comprising:
a blood glucose measurement device configured to generate blood glucose measurement values based on a blood sample, the blood glucose measurement device comprising:
a slot for receiving the blood sample, and
a user interface comprising a display device; and
an apparatus comprising:
a data storage adapted to store
a plurality of blood glucose measurement values generated by the blood glucose measurement device,
for each blood glucose measurement value an associated event tag,
for each blood glucose measurement value an associated time stamp,
an associated time range for tagging preselection for each of at least two meal events, and
a processor adapted to:
receive a new blood glucose measurement value from the data storage or from the blood glucose measurement device,
assign, using a clock unit, an associated time stamp to the new blood glucose measurement value, if an associated time stamp does not yet exist with the new blood glucose measurement value,
cause display, on the display device of the user interface, of one or more first graphical representations prompting a user of the blood glucose measurement system to select and/or confirm one of a "before meal" tag and an "after meal" tag with regard to the new blood glucose measurement value;
receive selection data containing information that the user has selected and/or confirmed one of a "before meal" tag and an "after meal" tag with regard to the new blood glucose measurement value, automatically determine an additional associated meal event tag referring to the one of the at least two meal events based at least partially on the received selection data and a comparison of the time stamp of the new blood glucose measurement value with the associated time ranges for tagging preselection of the at least two meal events stored in the data storage, store, in the data storage, each new blood glucose measurement value, its associated time stamp, its associated "before meal" tag or "after meal" tag, and its associated meal event tag;

determine a medicament dose suggestion based on each of the stored blood glucose measurement values, its associated "before meal" and "after meal" tag, and its associated meal event tag; and cause display, on the display device of the user interface, of one or more second graphical representations indicating the determined medicament dose suggestions to be used to assess the effectiveness of a prescribed treatment.

* * * * *

UNITED STATES PATENT AND TRADEMARK OFFICE
CERTIFICATE OF CORRECTION

PATENT NO. : 10,754,926 B2
APPLICATION NO. : 15/022146
DATED : August 25, 2020
INVENTOR(S) : Andrew Tubb Page 1 of 1

It is certified that error appears in the above-identified patent and that said Letters Patent is hereby corrected as shown below:

In the Claims

In Column 16, Line 19, Claim 8, delete "blood glucose system" and insert -- blood glucose measurement system --

In Column 16, Line 34, Claim 9, delete "system device," and insert -- system, --

In Column 17, Line 21 (approx.), Claim 12, delete "pre meal" and insert -- pre-meal --

In Column 17, Line 21 (approx.), Claim 12, delete "post meal" and insert -- post-meal --

Signed and Sealed this
Thirteenth Day of October, 2020

Andrei Iancu
*Director of the United States Patent and Trademark Office*